US011986652B1

(12) United States Patent
Ritzen et al.

(10) Patent No.: US 11,986,652 B1
(45) Date of Patent: May 21, 2024

(54) ELECTRICAL MUSCLE STIMULATION DEVICE AND METHODS FOR USE THEREOF

(71) Applicant: CJR IP Holdings LLC, Franklin, TN (US)

(72) Inventors: Jason Ritzen, Franklin, TN (US); Wiley Robinson, Nashville, TN (US)

(73) Assignee: CJR IP Holdings LLC, Franklin, TN (US)

( * ) Notice: Subject to any disclaimer, the term of this patent is extended or adjusted under 35 U.S.C. 154(b) by 432 days.

(21) Appl. No.: 16/869,168

(22) Filed: May 7, 2020

Related U.S. Application Data

(60) Provisional application No. 62/845,549, filed on May 9, 2019.

(51) Int. Cl.
| | |
|---|---|
| *A61N 1/36* | (2006.01) |
| *A63B 21/06* | (2006.01) |
| *A63B 22/00* | (2006.01) |
| *A63B 22/02* | (2006.01) |
| *A63B 22/04* | (2006.01) |
| *A63B 22/06* | (2006.01) |
| *A63B 22/20* | (2006.01) |
| *A63B 24/00* | (2006.01) |
| *A61F 7/00* | (2006.01) |
| *A61N 1/04* | (2006.01) |

(52) U.S. Cl.
CPC ..... *A61N 1/36003* (2013.01); *A61N 1/36031* (2017.08); *A63B 21/06* (2013.01); *A63B 22/0076* (2013.01); *A63B 22/02* (2013.01); *A63B 22/04* (2013.01); *A63B 22/0605* (2013.01); *A63B 22/0664* (2013.01); *A63B 22/20* (2013.01); *A63B 24/0062* (2013.01); *A61F 7/007* (2013.01); *A61F 7/0085* (2013.01); *A61N 1/0452* (2013.01); *A61N 1/36014* (2013.01); *A63B 2024/0093* (2013.01)

(58) Field of Classification Search
CPC ............ A61N 1/36003; A61N 1/36014; A61N 1/36031

See application file for complete search history.

(56) References Cited

U.S. PATENT DOCUMENTS

| | | | |
|---|---|---|---|
| 7,593,775 | B2 | 9/2009 | Campos et al. |
| 8,428,736 | B2 | 4/2013 | Schauer et al. |
| 9,230,064 | B2 * | 1/2016 | Yanev .................. A63B 21/002 |
| 10,765,863 | B2 * | 9/2020 | Perez ................. A61N 1/36014 |
| 11,389,652 | B2 * | 7/2022 | Toth ........................ A61N 1/36 |
| 2002/0077688 | A1 | 6/2002 | Kirkland |
| 2002/0077689 | A1 | 6/2002 | Kirkland |
| 2010/0185259 | A1 | 7/2010 | Shiba et al. |
| 2012/0172940 | A1 | 7/2012 | Wahls et al. |
| 2016/0114160 | A1 | 4/2016 | Scott |
| 2016/0303363 | A1 | 10/2016 | Girouard et al. |
| 2017/0173324 | A1 | 6/2017 | Horter et al. |
| 2017/0274199 | A1 | 9/2017 | Decker |

(Continued)

*Primary Examiner* — George R Evanisko
(74) *Attorney, Agent, or Firm* — NEO IP

(57) ABSTRACT

Electrical Muscle Stimulation (EMS) devices, methods, and systems for providing stimulating waveforms and stimulating electrical pulses to specific muscle groups and nerve areas of the body are provided. The EMS system includes at least one EMS device, at least one EMS control unit, at least one computing device, at least one server, at least one body sensor, and/or at least one environmental sensor.

12 Claims, 4 Drawing Sheets

(56) References Cited

U.S. PATENT DOCUMENTS

| | | |
|---|---|---|
| 2018/0028810 A1 | 2/2018 | Schwarz et al. |
| 2018/0036531 A1 | 2/2018 | Schwarz et al. |
| 2018/0056060 A1 | 3/2018 | Nishimura et al. |
| 2019/0001129 A1* | 1/2019 | Rosenbluth .............. A61N 1/08 |
| 2019/0247650 A1* | 8/2019 | Tran .................... A61N 1/3704 |

* cited by examiner

ELECTRICAL MUSCLE STIMULATION DEVICE AND METHODS FOR USE THEREOF

CROSS REFERENCES TO RELATED APPLICATIONS

This application is related to and claims priority from the following US patents and patent applications. This application claims the benefit of U.S. Provisional Patent Application No. 62/845,549, filed May 9, 2019, which is incorporated herein by reference in its entirety.

BACKGROUND OF THE INVENTION

1. Field of the Invention

The present invention relates to Electrical Muscle Stimulation (EMS) devices, methods, and systems for providing stimulating waveforms and stimulating electrical pulses to specific muscle groups of the body.

2. Description of the Prior Art

It is generally known in the prior art to provide EMS devices that apply a machine-generated electrical impulse through the skin and into the muscle. The electrical impulse has an intensity, a pulse duration, and a pulse width. In response to the electrical impulse, muscle contractions occur. An EMS device is generally a wearable item that includes a plurality of electrodes in a permanent or detachable manner. An electrical control unit delivers the electrical impulse to the EMS device.

Prior art patent documents include the following:

U.S. Publication No. 20180036531 for device, system and method for the transmission of stimuli by inventors Schwarz et al., filed Feb. 18, 2016 and published Feb. 8, 2018, is directed to a device and to a system and a method for transmitting stimuli to a user. The stimuli can include stimuli caused by electrical muscle stimulation or haptic stimuli such as vibrations. The system simplifies the use of the corresponding stimuli inter alia in that parameters can be measured during the use and the type and specificity of the stimuli can be changed depending on the measured parameters. The systems, devices and methods are particularly suitable for use in sports, U.S. Publication No. 20180028810 for system for controlling stimulation impulses by inventors Schwarz et al., filed Feb. 18, 2016 and published Feb. 1, 2018, is directed to a system for controlling stimulation impulses, including at least one control unit and one item of clothing having a plurality of electrodes for electro-stimulation. The control unit is configured to carry out electro-stimulation with defined parameters at different electrodes and, during a training session, different parameters can be produced at different electrodes by said control unit.

U.S. Publication No. 20180056060 for control device for electrical stimulation apparatus, electrical stimulation apparatus, and pedaling exercise system by inventors Nishimura et al., filed Jul. 13, 2017 and published Mar. 1, 2018, is directed to a control device for an electrical stimulation apparatus including a control section that adjusts an output of an electrode. The electrode gives electrical stimulation to a predetermined part of a body doing a pedaling exercise. The predetermined part is at least one of a leg and an arm. The control section adjusts the output of the electrode in such a way that the electrical stimulation is given to the predetermined part in relation to an exercise unit of the pedaling exercise. Furthermore, the control section adjusts strength of the electrical stimulation related to the exercise unit, in accordance with an amount of a physical activity of the body during the pedaling exercise. In this way, electrical stimulation can be given to a predetermined part in a variable manner during the pedaling exercise.

U.S. Publication No. 20170274199 for EMS stimulation current transmission element and EMS garment equipped with the EMS stimulation current transmission element by inventor Decker, filed Jun. 8, 2017 and published Sep. 28, 2017, is directed to an EMS stimulation current transmission element for an EMS garment including a planar current transmission region of an EMS electrode for transmitting EMS stimuli to the living body, which contains a number of two-dimensionally arranged linear current conductor strand sections and is connected, via a further number of linear current conductor strand sections, to a connection point that is in particular spaced apart from the current transmission region, at which connection point the EMS stimulation current transmission element can be connected to an EMS stimulation current production unit, in order to load the current transmission region with an EMS stimulation current shaped by the EMS stimulus current production unit from a current drawn from a current source to form a pulse sequence and/or to form an alternating current. The current transmission region has a single linear current conductor strand section. An EMS garment has an EMS stimulation current transmission element.

U.S. Publication No. 20170173324 for EMS exercise device, EMS electrode, EMS garment, EMS stimulus generating unit, EMS signal cable, and EMS undergarment for an EMS exercise device, and method for operating the EMS exercise device by inventors Horter et al., filed Mar. 5, 2017 and published Jun. 22, 2017, is directed to an EMS exercise device which includes EMS electrodes and at least one sacrificial anode, preferably a dedicated sacrificial anode for each EMS electrode. The at least one sacrificial anode is connected to the EMS electrodes in an electrically conductive manner in order to protect the EMS electrodes and/or other elements in the electrically conductive connections from corrosion. In addition, an EMS electrode with a sacrificial anode, an EMS garment a sacrificial anode, an EMS signal cable a sacrificial anode, an EMS pulse generating unit a sacrificial anode, and an EMS undergarment with a sacrificial anode for an EMS exercise device are provided, and a method for operating an EMS exercise device, for which a sacrificial anode is provided.

U.S. Publication No. 20160303363 for NMES garment by inventors Girouard et al., filed Mar. 17, 2016 and published Oct. 20, 2016, is directed to apparatuses, methods, and systems for simulating low and/or high intensity exercise. More particularly, the invention relates to an exercise mimetic device for simulating low and/or high intensity exercise using low intensity electrical stimulation to generate low intensity muscle contractions such as a wearable garment that preferably imitates exercise by eliciting low grade muscle contractions in several of the larger skeletal muscle groups in the body. The apparatus of various embodiments of the invention is a neuromuscular electrostimulation (NMES) device/garment with a control unit that is wirelessly connected to and controls a stimulator unit that generates and transmits a low intensity electrical stimulation within certain unique parameters. In various embodiments, the NMES device/garment is for treating conditions including but not limited to obesity, obesity related conditions such as diabetes, muscle toning, and/or other conditions benefitted by exercise. In various embodiments, the NMES device/ garment is an over the counter (OTC) NMES device/ garment.

U.S. Publication No. 20160114160 for electro-muscular stimulation system by inventor Scott, filed Jul. 30, 2015 and published Apr. 28, 2016, is directed to an electro-muscular stimulation system for the electric stimulation of certain muscle groups of a user. The system comprises a compression suit, control unit, and battery pack. The compression suit is wearable by the user and comprises an EMS device and an accelerometer. The control unit is in electric communication with the EMS device and the accelerometer. The control unit is configured to receive a data input and convert the data input into an electric-stimulation signal that is sent to the EMS device. The accelerometer is configured to provide feedback data to the control unit. The battery pack is configured to provide power to the EMS device and the accelerometer.

U.S. Pat. No. 8,428,736 for muscle stimulator and control methods therefor by inventors Schauer et al., filed Feb. 4, 2011 and issued Apr. 23, 2013, is directed to an apparatus and methods for muscle stimulation and control of muscle stimulators. In at least one embodiment, an electrical muscle stimulator includes a belt having a plurality of stimulator pads, a pulse width modulator controlled by a feedback loop, the PWM providing output to control voltages of the stimulator pads, and a control unit to control the PWM and feedback loop. In various embodiments, the control unit monitors PWM output values during a rest phase of a cycle of the muscle stimulator, provides a contraction phase, and following a sag after the contraction phase, uses PWM values from the rest phase to set a voltage for a subsequent rest phase of a next cycle.

U.S. Publication No. 20120172940 for therapeutic garment by inventors Wahls et al., filed Nov. 30, 2011 and published Jul. 5, 2012, is directed to a modular therapeutic garment having electrodes integral with the garment and treatment permitted by such garment. The therapeutic garment can comprise a compression knit fabric material, and an array of electrodes integral with the compression knit fabric material. The compression knit fabric material can exert pressures within a range including values suitable for clinical treatment. The array of electrodes can be arranged to overlie specific portions of a subject, such as muscle groups or other body parts. Each electrode of the array of electrode can be formed of a conductive knit fabric material. The conductive knit fabric material can enclose a liquid absorptive material. A method for treating a musculoskeletal dysfunction with the therapeutic garment also is provided. The method also can be effective at improving musculoskeletal condition of healthy subjects.

U.S. Publication No. 20100185259 for garment for electrically stimulating muscles by inventors Shiba et al., filed Jun. 25, 2008 and published Jul. 22, 2010, is directed to a garment for electrically stimulating muscles to be used for, e.g., rehabilitation or exercise whereby an electrode can be conveniently provided at such a position as allowing the electrode to stimulate the nerve-muscular junction of a muscle to be moved in toning up the muscle through electrical stimulation on the muscle by taking advantage of the muscular contraction caused by electrically stimulating the muscle. A garment for electrically stimulating muscles comprises a garment body, a required number of openings which are provided in the garment body in such a manner that each opening is located at the nerve-muscular junction or in the vicinity of the nerve-muscular junction of a muscle to be moved in the case where a wearer wears the garment body, and electrodes provided at the respective openings in such a manner that each electrode located on the skin surface at the nerve-muscular junction or in the vicinity of the nerve-muscular junction of a muscle in the case where a wearer wears the garment body.

U.S. Pat. No. 7,593,775 for sports equipment with resonant muscle stimulator for developing muscle strength by inventors Campos et al., filed Feb. 27, 2004 and issued Sep. 22, 2009, is directed to a method and apparatus including a therapeutic or developmental instrument that includes hardware and/or software for stimulating a muscle. Such an instrument may comprise, for instance, a golf club, a baseball bat, a lacrosse stick, a tennis racquet or a hockey stick, among other sports-related instruments. Still other suitable instruments may include a writing instrument, such as a pen. In the case of a golf club, a muscle of a user may be stimulated by the instrument as the golfer practices her swing. Combining such muscle stimulation with the act of practicing the movement of the swing has a synergistic effect of training the muscle as it builds strength. Similarly, a partial paralytic may regain strength in their hand by holding and writing with a pen configured to transcutaneously deliver a stimulating signal. Where desired, the instrument may include at least one electrode configured to deliver a stimulating signal to the holder of the instrument. In another or the same embodiment, wired electrodes may extend from the instrument or an adjacent signal generator to the holder of the instrument. This configuration may allow other, targeted muscles to be concurrently stimulated while the user manipulates the instrument.

U.S. Publication No. 20020077689 for electrode positioning bodysuit by inventor Kirkland, filed Aug. 15, 2001 and published Jun. 20, 2002, is directed to a suit of a flexible elastomeric material that fits snug to the body used in conjunction with an electrical muscle and/or nerve stimulation device. The suit is specifically structured to advantageously position electrode pads at predetermined positions on the body corresponding with different muscle groups and is provided with pockets, rivets, thread, or adhesive for holding the electrode pads at the predetermined positions. The electrode pads are interconnected by wires, which are routed through seams in the arms, legs, back, and chest of the suit. The wires exit at the waist and lead to an interface connector that connects to output connector of the stimulation device. A color-coded connection between the output connector of the stimulation device and the interface connector enables selectively directing of stimulation signals to one or more of the electrode pads to thereby target specific muscle groups of the body. The stimulation device permits selective adjustment of the duration and intensity of the signal and electrical pulse delivered to specific muscle groups and/or nerve areas.

U.S. Publication No. 20020077688 for electrode-positioning body garment by inventor Kirkland, filed Dec. 14, 2001 and published Jun. 20, 2002, is directed to a garment made of a flexible elastic material that fits snug to the body and is used in conjunction with an electrical muscle and/or nerve stimulation device. The garment is specifically structured to advantageously position electrode pads at predetermined positions on the body corresponding with different muscle or nerve groups. In one embodiment, wires connecting to the electrodes lead to an interface connector that connects to an external controller of the stimulation device. Alternatively, the entire stimulation device, including the controller, is carried on the garment. The controller enables the user to selectively direct stimulation signals to one or more of the electrode pads in order to target specific muscle or nerve groups of the body. The controller further permits selective adjustment of the duration and intensity of the signal and electrical pulse delivered to the specific muscle groups and/or nerve areas. In a further embodiment, the garment is in the form of a sleeve or wrap and is structured to cover a specific area of the body to be treated, such as the arms, legs, abdomen, chest or face.

SUMMARY OF THE INVENTION

The present invention relates to devices, methods, and systems for electrically stimulating muscles. More specifically, the present invention relates to an EMS device and an EMS control unit used for exercise and/or rehabilitation using EMS to train muscles using muscular contraction by electrically stimulating muscles.

It is an object of this invention to provide an electrical muscle stimulation system that adapts to sensor data to improve exercise programs.

In one embodiment, an electrical muscle stimulation system including at least one electrical muscle stimulation device, at least one sensor, an electrical stimulation control unit a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein the server is in network communication with the computing device, the at least one sensor, and the at least one electrical muscle stimulation device, and wherein the server is operable to store data from the at least one sensor.

In another embodiment, the present invention includes an electrical muscle stimulation system including at least one electrical muscle stimulation device, at least one sensor, an electrical stimulation control unit, a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein one or more of the at least one electrical muscle stimulation device is configured to provide heating and/or cooling, wherein the one or more of the at least one electrical muscle stimulation device is configured to adjust heating and/or cooling levels in response to data from one or more of the at least one sensor, wherein the server is in network communication with the computing device, the at least one sensor, and the at least one electrical muscle stimulation device, and wherein the electrical stimulation control unit is configured to update the training program in real time and/or near real time in response to data received from one or more of the at least one sensor.

In yet another embodiment, the present invention includes an electrical muscle stimulation exercise system including at least one electrical muscle stimulation device, an exercise machine, at least one sensor, an electrical stimulation control unit, a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein the electrical stimulation control unit is embedded in the exercise device, wherein the electrical stimulation control unit is configured to store data captured from the at least one sensor, wherein the electrical stimulation control unit is configured to update the training program in real time and/or near real time in response to data received from one or more of the at least one sensor, and wherein the server is in network communication with the computing device, the at least one sensor, and the at least one electrical muscle stimulation device.

These and other aspects of the present invention will become apparent to those skilled in the art after a reading of the following description of the preferred embodiment when considered with the drawings, as they support the claimed invention.

DETAILED DESCRIPTION

Figure 1:
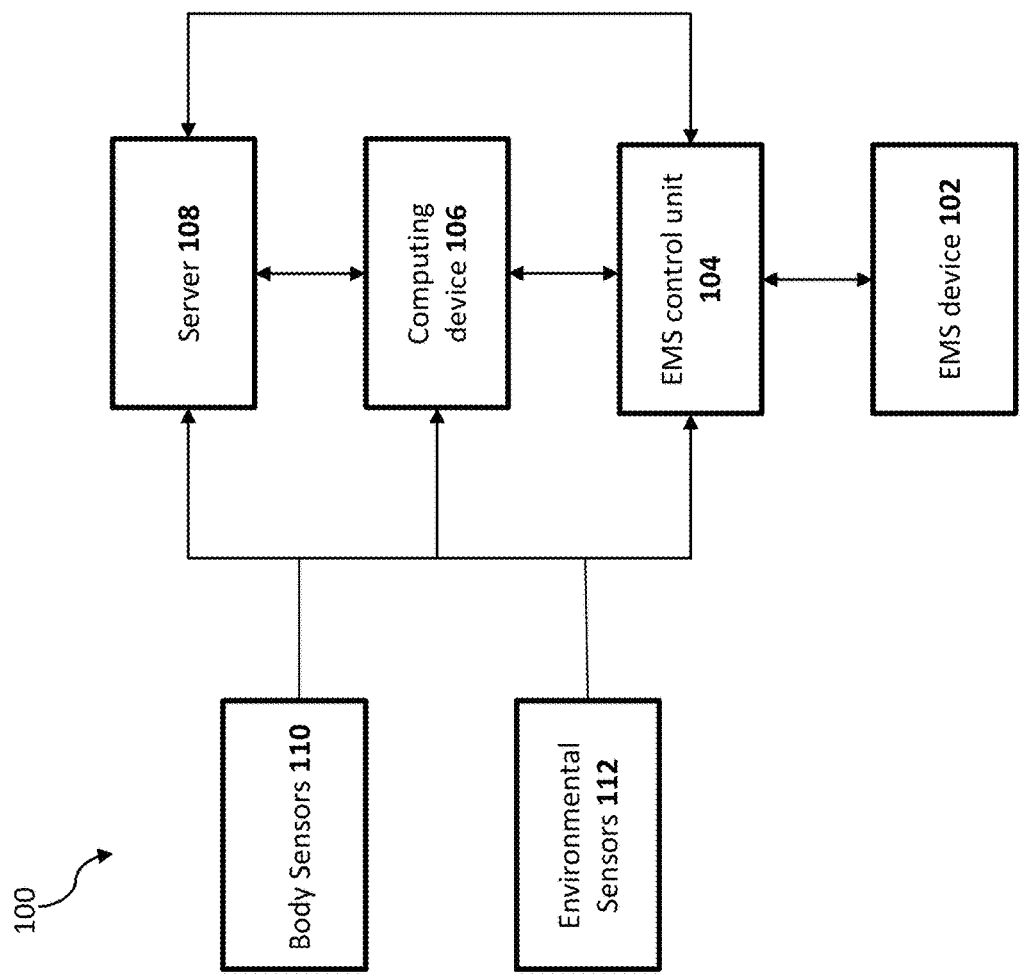
FIG. 1 is a block diagram of an EMS system according to one embodiment of the present invention.

The present invention is generally directed to EMS devices, methods, and systems for providing stimulating waveform and electrical pulses to specific muscle groups of the body through an EMS device.

In one embodiment, an electrical muscle stimulation system including at least one electrical muscle stimulation device, at least one sensor, an electrical stimulation control unit a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein the server is in network communication with the computing device, the at least one sensor, and the at least one electrical muscle stimulation device, and wherein the server is operable to store data from the at least one sensor. The local storage includes user profile data, historical subjective data, historical objective data, and/or historical environmental data. The electrical muscle stimulation system further includes at least one wearable device, wherein one or more of the at least one sensor is incorporated into the at least one wearable device. The at least one body sensor includes at least one heart sensor, at least one respiration sensor, at least one body composition sensor, at least one movement sensor, at least one electromyography sensor, at least one pulse oximetry sensor, at least one body temperature sensor, at least one analyte sensor, at least one pH sensor, at least one blood pressure sensor, at least one electrodermal activity sensor, at least one weight sensor, at least one hydration sensor, at least one GPS sensor, at least one pressure sensor, and/or at least one spinal sensor. The at least one environmental sensor includes a temperature sensor, a humidity sensor, and/or a motion sensor. The electrical stimulation control unit is configured to transmit an electrical impulse signal to one or more of the at least one electrode, wherein the electrical stimulation control unit is configured to change an impulse signal type, an impulse signal frequency, an impulse signal intensity, an impulse signal polarity, an impulse signal duration, and/or a rest period between impulses. The electrical stimulation control unit is operable to automatically adjust the electrical impulse signal in response to data received from one or more of the at least one sensor. The electrical stimulation control unit includes a machine learning component, wherein the machine learning component is configured to recommend the training program based on data stored in the local storage. The server includes a modeling engine, wherein the modeling engine includes artificial intelligence algorithms, wherein the server is operable to collect data from a third party, and wherein the server is configured to model the training program based on data from the local storage and/or the third party. One or more of the at least one electrical muscle stimulation device is configured to provide heating and/or cooling, and wherein the one or more of the at least one electrical muscle stimulation device is configured to automatically adjust heating and/or cooling levels in response to data received from the at least one sensor. The server includes a reasoning engine, wherein the reasoning engine includes artificial intelligence algorithms, and wherein the reasoning engine is configured to generate a reasoning model using data on the local storage. The server is configured to determine an effectiveness of the training program, and wherein the effectiveness is based on a change in muscle strength, power, flexibility, endurance, balance, speed, agility, and/or cardiovascular strength. The electrical stimulation control unit is configured to update the training program in real time and/or near real time in response to data received from the at least one sensor. The training program is a sport specific training program, wherein the electrical stimulation control unit is configured to generate the sport specific training program, wherein the sport specific training program targets at least one muscle and/or at least one muscle group, wherein the at least one electrical muscle stimulation device is configured to stimulate the at least one muscle and/or the at least one muscle group, and wherein the electrical stimulation control unit is configured to automatically adjust the sport specific training program in response to data received from one or more of the at least one sensor.

In another embodiment, the present invention includes an electrical muscle stimulation system including at least one electrical muscle stimulation device, at least one sensor, an electrical stimulation control unit, a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein one or more of the at least one electrical muscle stimulation device is configured to provide heating and/or cooling, wherein the one or more of the at least one electrical muscle stimulation device is configured to adjust heating and/or cooling levels in response to data from one or more of the at least one sensor, wherein the server is in network communication with the computing device, the at least one sensor, and the at least one electrical muscle stimulation device, and wherein the electrical stimulation control unit is configured to update the training program in real time and/or near real time in response to data received from one or more of the at least one sensor. The at least one electrical muscle stimulation device includes a one-piece suit. The at least one body sensor includes at least one heart sensor, at least one respiration sensor, at least one body composition sensor, at least one accelerometer, at least one electromyography sensor, at least one pulse oximeter, at least one analyte sensor, at least one pH sensor, at least one body weight sensor, at least one GPS sensor, and/or at least one spinal sensor.

In yet another embodiment, the present invention includes an electrical muscle stimulation exercise system including at least one electrical muscle stimulation device, an exercise machine, at least one sensor, an electrical stimulation control unit, a computing device, and a server, wherein each of the at least one electrical muscle stimulation device includes at least one electrode, wherein the at least one sensor includes at least one body sensor and/or at least one environmental sensor, wherein the electrical stimulation control unit includes at least one processor, an analytics engine, a user interface, local storage, and a transceiver, wherein the local storage includes a training program, wherein the electrical stimulation control unit is in network communication with the at least one electrical muscle stimulation device, the server, the at least one sensor, and the computing device, wherein the electrical stimulation control unit is embedded in the exercise device, wherein the electrical stimulation control unit is configured to store data captured from the at least one sensor, wherein the electrical stimulation control unit is configured to update the training program in real time and/or near real time in response to data received from one or more of the at least one sensor, and wherein the server is in network communication with the computing device, the at least one sensor, and the at least one electrical muscle stimulation device. The exercise machine is an elliptical, a stair climber, a bicycle, a vertical climber, a weight machine, a treadmill, a ski machine, a rowing machine, a glider, an incline trainer, a resistance machine, or a Pilates machine, wherein the exercise machine includes at least one setting, wherein the at least one setting includes speed and/or resistance, and wherein the electrical stimulation control unit is configured to automatically adjust the at least one setting based on data captured from one or more of the at least one sensor. The electrical stimulation control unit includes a machine learning component, wherein the machine learning component is configured to recommend the training program based on the data in the local storage.

None of the prior art discloses an electrical muscle stimulation system that is operable to adapt to sensor data and update an exercise training program.

Referring now to the drawings in general, the illustrations are for the purpose of describing one or more preferred embodiments of the invention and are not intended to limit the invention thereto.

System

FIG. 1 illustrates one embodiment of the EMS system. The EMS system 100 includes at least one EMS device 102, at least one EMS control unit 104, at least one computing device 106, at least one server 108, at least one body sensor 110, and/or at least one environmental sensor 112. Each of the at least one EMS device 102 is wearable by a user and includes at least one electrode for stimulating at least one muscle and/or at least one muscle group. The at least one EMS device 102 is in network communication with the at least one EMS control unit 104. In one embodiment, the at least one EMS device 102 is in wireless network communication with the at least one EMS control unit 104. The wireless communication is, by way of example and not limitation, radio frequency (RF), BLUETOOTH, ZIGBEE, WI-FI, wireless local area networking, near field communication (NFC), or other similar commercially utilized standards. Alternatively, the at least one EMS device 102 is in wired network communication with the at least one EMS control unit 104 via at least one cable (e.g., universal serial bus (USB), FIREWIRE®, or equivalent).

The at least one EMS control unit 104 is in network communication with the at least one computing device 106 (e.g., smartphone, tablet, laptop computer, desktop computer). The at least one EMS control unit 104 is in network communication with the at least one server 108. In a preferred embodiment, the at least one EMS control unit 104 is in wireless network communication with the at least one computing device 106 and the at least one server 108. Alternatively, the at least one EMS control unit 104 is in wired network communication with the at least one computing device 106 and/or the at least one server 108.

The at least one computing device 106 is in network communication with the at least one server 108. The at least one computing device 106 is preferably in wireless network communication with the at least one server 108. Alternatively, the at least one computing device 106 is in wired network communication with the at least one server 108.

The system further includes at least one body sensor 110 and/or at least one environmental sensor 112. In a preferred embodiment, the at least one body sensor 110 and/or at least one environmental sensor 112 is in network communication with the at least one EMS control unit 104, the at least one computing device 106, and/or the at least one server 108. In a preferred embodiment, the at least one body sensor 110 and/or at least one environmental sensor 112 is in wireless network communication with the at least one EMS control unit 104, the at least one computing device 106, and/or the at least one server 108. Alternatively, the at least one body sensor 110 and/or at least one environmental sensor 112 is in wired network communication with the at least one EMS control unit 104, the at least one computing device 106, and/or the at least one server 108. In one embodiment, one or more of the at least one body sensor 110 and/or one or more of the at least one environmental sensor 112 is incorporated into the at least one EMS device 102 and/or the at least one EMS control unit 104. In another embodiment, one or more of the at least one body sensor 110 and/or one or more of the at least one environmental sensor 112 is operable to transmit data to the at least one EMS control unit 104, the at least one computing device 106, and/or the at least one server 108 in real time and/or near real time.

Figure 2:
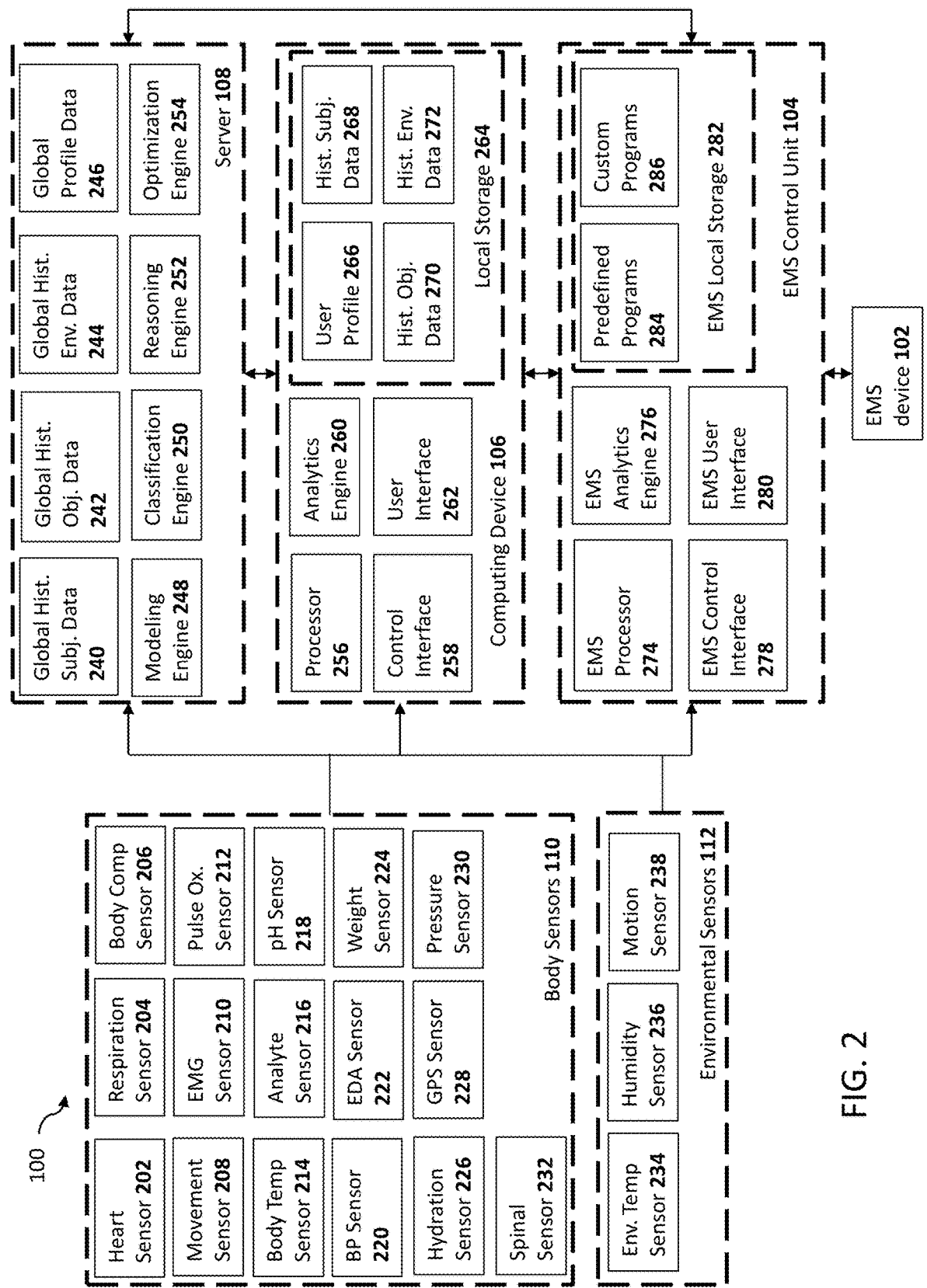
FIG. 2 is a detailed block diagram of the EMS system in FIG. 1.

FIG. 2 is a detailed block diagram of the EMS system of FIG. 1. As previously described, the EMS system 100 includes at least one EMS device 102, at least one EMS control unit 104, at least one computing device 106, at least one server 108, at least one body sensor 110, and/or at least one environmental sensor 112.

The at least one EMS control unit 104 includes at least one EMS processor 274, an EMS analytics engine 276, an EMS control interface 278, an EMS user interface 280, and an EMS local storage 282. The EMS local storage 282 includes at least one predefined program 284 and/or at least one custom program 286.

The at least one computing device 106 includes at least one processor 256, an analytics engine 258, a control interface 260, a user interface 262, and a local storage 264. The local storage 264 includes a user profile 266, historical subjective data 268, historical objective data 270, and historical environmental data 272. The user profile 266 stores preferences and information about the user, including, but not limited to, age, weight, height, gender, medical history (e.g., injuries, medications, diseases), and/or fitness (e.g., fitness level, fitness activities, fitness goals). The historical subjective data 268 includes mood, emotional stress, general stress, perceived exertion, perceived soreness, perceived recovery, and fatigue level. The historical objective data 270 includes information gathered from the body sensors 110. The historical environmental data 272 includes information gathered from the environmental sensors 112.

In one embodiment, the historical subjective data 268 includes information obtained from the Profile of Mood States (POMS)(including derivatives of the POMS), Recovery Stress Questionnaire for Athletes (RESTQ-S), Daily Analyses of Life Demands of Athletes (DALDA), the overtraining questionnaire of the Societe Francaise de Medecine du Sport (SFMS), State-Trait Anxiety Inventory (STAI), Perceived Stress Scale (PSS), Multi-Component Training Distress Scale (MTDS), Competitive State Anxiety Inventory-2 (CSAI-2), Derogatis Symptom Checklist (DSC), State-Trait Personality Inventory (STPI), and/or a mood questionnaire by Choi and Salmon (Mood). The POMS is described in McNair et al. (1981), POMS manual, $2^{nd}$ ed San Diego, CA: Education and Industrial Testing Service, which is incorporated herein by reference in its entirety. The derivatives of the POMS are described in Terry et al. (1991), "Development and validation of a mood measure for adolescents." *J Sports Sci*, (17): 861-872, which is incorporated herein by reference in its entirety. The RESTQ-S is described in Kellmann et al. (2001), Recovery-stress questionnaire for athletes: user manual, Champaign, IL: Human Kinetics, which is incorporated herein by reference in its entirety. The DALDA is described in Rushall B S (1990), A tool for measuring stress tolerance in elite athletes, *J Appl Sport Psychol;* 2: 51-66, which is incorporated herein by reference in its entirety. The SFMS is described in Legros P. (1993), "Le surentrainement: diagnostic des manifestations psychocomportementales precoces," *Sci Sports*, (8): 71-74, which is incorporated herein by reference in its entirety. The STAI is described in Spielberger et al. (1970), Manual for the state-trait anxiety inventory, Palo Alto, CA: Consulting Psychologists Press, which is incorporated herein by reference in its entirety. The PSS is described in Cohen et al. (1983), A global measure of perceived stress, *J Health Soc Behav;* (24):385-396, which is incorporated herein by reference in its entirety. The MTDS is described in Main L, Grove J R, A multi-component assessment model for monitoring training distress among athletes, Eur J Sport Sci 2009; 9:195-202, which is incorporated herein by reference in its entirety. The CSAI-2 is described in Martens R et al., Development and validation of the competitive sports anxiety inventory 2, In: Martens R, Vealey R S, Burton D., eds, Competitive anxiety in sport, Champaign, IL: Human kinetics, 1990: 117-78, which is incorporated herein by reference in its entirety. The DSC is described in Derogatis L R, SCL-90: administration, scoring and procedures manual for the R(evised) version, Baltimore, MD: Johns Hopkins University School of Medicine, 1977, which is incorporated herein by reference in its entirety. The STPI is described in Spielberger C D, et al., The preliminary manual for the State-Trait Personality Inventory [Unpublished manual], Tampa: University of South Florida, 1979, which is incorporated herein by reference in its entirety. The Mood is described in Choi P Y, Salmon P, Symptom changes across the menstrual cycle in competitive sportswomen, exercisers and sedentary women, Br J Clin Psychol 1995; 34:447-60, which is incorporated herein by reference in its entirety.

The at least one server 108 includes global historical subjective data 240, global historical objective data 242, global historical environmental data 244, global profile data 246, a modeling engine 248, a classification engine 250, a reasoning engine 252, and an optimization engine 254. The global historical objective data 240, the global historical subjective data 242, the global historical environmental data 244, and the global profile data 246 include data from multiple users.

The at least one body sensor 110 includes at least one heart sensor 202, a respiration sensor 204, at least one body composition sensor 206, at least one movement sensor 208, at least one electromyography sensor 210, a pulse oximetry sensor 212, a body temperature sensor 214, at least one analyte sensor 216, a pH sensor 218, a blood pressure sensor 220, an electrodermal activity sensor 222, a weight sensor 224, a hydration sensor 226, a GPS sensor 228, a pressure sensor 230, and/or a spinal sensor 232.

The at least one environmental sensor 112 includes an environmental temperature sensor 234, a humidity sensor 236, and/or at least one motion sensor 238. In one embodiment, the environmental temperature sensor 234, the humidity sensor 236, and/or the motion sensor 238 are incorporated into an automation system (e.g., AMAZON® ALEXA®, APPLE® HOMEKIT™, GOOGLE® HOME™, IF THIS THEN THAT® (IFTTT®), NEST®).

EMS Device

The system includes at least one EMS device wearable by user that includes a plurality of electrodes to stimulate at least one muscle and/or at least one muscle group. In one embodiment, the at least one EMS device is a one-piece body suit. In another embodiment, the at least one EMS device is a two-piece body suit, including an upper body component and a lower body component. In yet another embodiment, the at least one EMS device is formed of at least one piece, wherein the at least one piece is sized to cover at least one muscle group of the human body (e.g., covering one or both legs, the chest, one or both arms, the torso). In one embodiment, the plurality of electrodes in incorporated into a textile.

In one embodiment, the EMS device is formed of an elastomeric material (e.g., neoprene, spandex). Permanent or detachable electrodes are located on or embedded within the EMS device. Each electrode and/or group of electrodes correspond to a particular muscle and/or muscle group. An example of an EMS device is disclosed in U.S. Publication No. 20160120475, which is incorporated herein by reference in its entirety. Wiring from the plurality of electrodes is preferably routed through seams of the EMS device to an exterior surface. In one example, the EMS device is a one-piece suit and wiring from the electrodes is routed from the upper limbs, lower limbs, and chest to the waist of the one-piece suit. The wiring is preferably electrically connected to a cable that connects the EMS device to the control unit.

In one embodiment, the wires connecting the EMS device to the EMS control unit are color coded. Each color corresponds to a specific muscle group on the human body. For example, purple corresponds to electrodes on a user's chest, yellow corresponds to electrodes on a user's arms, and orange corresponds to electrodes on a user's shoulders. This enables a user to easily identify which muscle groups are being targeted in their current training program.

In one embodiment, the EMS device includes at least one sensor (e.g., body sensor, environmental sensor). In a preferred embodiment, one or more of the at least one sensor is operable to transmit data to the control unit, the at least one computing device, and/or the at least one remote server in real time and/or near real time. In one embodiment, data from the at least one sensor (e.g., real-time data) is incorporated into an existing or a new training session as an indicator of a user's performance and/or status.

In another embodiment, the EMS device is operable to change its thermal properties to adapt to the environment and/or the user's body. This function is beneficial in providing training programs that can simulate real-world conditions (e.g. temperature/weather). This includes the ability to adjust the heating and/or cooling levels of the EMS device. In one embodiment, the EMS device uses water to heat and/or cool the device. The water is heated and/or cooled using a thermoelectric device attached to the EMS device. In another embodiment, the EMS device incorporates heating coils to heat the device.

In one embodiment, at least one connector is between at least one electrode of the EMS device and the EMS control unit. In another embodiment, the EMS device is powered by the EMS control unit. Alternatively, the EMS device is powered by at least one battery (e.g., rechargeable battery pack).

EMS Control Unit

The EMS device is specifically structured to be used in conjunction with an EMS control unit. In one embodiment, the EMS control unit has a housing and at least one EMS processor. In another embodiment, the EMS control unit includes an EMS interface. The EMS control unit preferably includes at least one transceiver to receive and transmit data. The EMS control unit is in network communication with a server and/or a computing device. The EMS control unit also includes a connector, allowing the control unit to electrically communicate with the EMS device.

The EMS control unit is also configured to deliver an electrical impulse to at least one electrode of the plurality of electrodes in the EMS device. During a training session, the EMS control unit is operable to vary characteristics of the electrical impulse (e.g., pulse width, duration, type). In one embodiment, a training session comprises a cycle of several minutes, wherein phases of stimulation of, for example, 4 seconds alternate with rest periods of the same duration. The electrical impulse is preferably a square, a rectangular, a triangular, or a sawtooth waveform. The EMS control unit is operable to vary electrical impulse characteristics, including, but not limited to, impulse type, frequency, intensity, polarity, duration, and rest period between impulses. In this way, the at least one EMS processor is configured to vary the electrical impulse characteristics for specific exercises and/or muscle groups.

The EMS control unit preferably includes an EMS control interface. In one embodiment, the EMS control interface is a touch screen. In another embodiment, the EMS control interface includes adjustable knobs, sliders, and/or dials. In yet another embodiment, the EMS control interface includes at least one light emitting diode (LED).

The EMS control unit is preferably operable to display data from the body sensors and/or the environmental sensors. In certain embodiments, the EMS control unit is operable to automatically adjust the electrical stimulation signal (e.g., pulse characteristics) that is sent to the EMS device as a result of the data received from the body sensors and/or the environmental sensors. In other embodiments, activation of the electric stimulation signal is triggered by the data received from the body sensors and/or the environmental sensors.

In a preferred embodiment, the EMS processor includes a machine learning component. This machine learning component incorporates a user's historical data, user profile data, a user's desired training program, a trainer's recommended training program, a user's specific fitness goal(s), data from body sensors (e.g., real-time data), and/or data from environmental sensors (e.g., real-time data) to determine the most efficient training program(s) to perform and make a recommendation. In one example, the AI-component recommendation conflicts with the user's desired training program and/or the trainer's recommended training program. In the event of a conflict, if a user selects their own training program and/or the trainer's recommended training program, the AI-component preferably recommends a follow-up program.

In another embodiment, the machine learning component automatically adjusts at least one setting on the EMS control device (e.g., impulse type, frequency, intensity, polarity, duration, rest period between impulses) based on a user's real-time data (e.g., body sensors) and/or progress in the user's current training program.

In yet another embodiment, the machine learning component recommends dietary guidelines based on a user's historical data, a user's profile, completed training programs, and/or a user's specific fitness goal(s). This recommendation serves as a supplement to a user's training performed while wearing the EMS device.

Body Sensors

The heart sensor 202 is preferably incorporated into a wearable device (e.g., APPLE WATCH®, FITBIT®, JAWBONE®). Alternatively, the heart sensor 202 is attached to the user with a chest strap. In another embodiment, the heart sensor 202 is incorporated into a patch or a bandage. In yet another embodiment, the heart sensor is incorporated into the EMS device. A heart rate is determined using electrocardiography, pulse oximetry, ballistocardiography, or seismocardiography. In one embodiment, the heart sensor 202 measures heart rate variability (HRV). HRV is a measurement of the variation in time intervals between heartbeats. A high HRV measurement is indicative of less stress (e.g., from exercise, psychological events), while a low HRV measurement is indicative of more stress. In one embodiment, a Poincare plot is generated to display HRV on a device such as a smartphone. In another embodiment, the heart sensor is operable to take an electrocardiogram (ECG) reading (e.g., via APPLE WATCH®).

The respiration sensor 204 measures a respiratory rate. In one embodiment, the respiration sensor 204 is incorporated into a wearable device. In another embodiment, the respiration sensor 204 is a sound sensor. Alternatively, the respiratory rate is estimated from an electrocardiogram, a photoplethysmogram (e.g., a pulse oximeter), and/or an accelerometer. In yet another embodiment, the respiratory sensor 204 uses a non-contact motion sensor to monitor respiration. In still another embodiment, the respiration sensor 204 measures a maximum rate of oxygen consumption ($VO_2$ max).

The body composition sensor 206 is preferably a bioelectrical impedance device (e.g., INBODY™ 770). Examples of a bioelectrical impedance device include U.S. Patent Publication Nos. 20160089082, 20160120475, 20180098735, and 20180020945, each of which is incorporated herein by reference in its entirety. In one embodiment, the body composition sensor 206 is incorporated into a smart scale (e.g., FITBIT® ARIA®, NOKIA® Body+, GARMIN® INDEX™, UNDER ARMOUR® Scale, PIVOTAL LIVING® Smart Scale, IHEALTH® Core). Alternatively, the body composition sensor 206 is a handheld device. In another embodiment, the body composition sensor 206 is a three-dimensional (3D) body scanner (e.g., STYKU®). Examples of a 3D body scanner include U.S. Patent Publication Nos. 20180144237, 20160088284, and 20160078663, each of which is incorporated herein by reference in its entirety. In yet another embodiment, the body composition sensor 206 is an air displacement plethysmograph (e.g., BOD POD). Examples of an air displacement plethysmograph include U.S. Pat. Nos. 7,022,087, 6,778, 926, and 6,910,373, each of which is incorporated herein by reference in its entirety. In still another embodiment, the body composition sensor 206 is a dual-emission X-ray absorptiometry (DEXA) scan. Alternatively, the body composition sensor 206 is a digital body fat caliper. In other embodiments, body composition is determined using hydrostatic weighing, a measuring tape, and/or mechanical body fat caliper. Measurements from the hydrostatic weighing, the measuring tape, and/or the mechanical body fat caliper are entered (e.g., via the computing device) and transmitted (e.g., to the server).

The movement sensor 208 is an accelerometer and/or a gyroscope. In one embodiment, the accelerometer and/or the gyroscope is incorporated into the EMS device. In another embodiment, the accelerometer and/or the gyroscope is incorporated into a wearable device (e.g., FITBIT®, JAWBONE®, ACTIGRAPH™). In yet another embodiment, the accelerometer and/or the gyroscope is incorporated into a smartphone.

The electromyography (EMG) sensor 210 records the electrical activity produced by skeletal muscles. Impulses are recorded by attaching electrodes to the skin surface over the muscle. In one embodiment, at least one EMG sensor 210 is incorporated into the EMS device.

The pulse oximeter sensor 212 monitors oxygen saturation. In one embodiment, the pulse oximeter sensor 212 is worn on a finger, a toe, or an ear. In another embodiment, the pulse oximeter sensor 212 is incorporated into a patch or a bandage. The pulse oximeter sensor 212 is preferably wireless. Alternatively, the pulse oximeter sensor 212 is wired. In one embodiment, the pulse oximeter sensor 212 is connected by a wire to a wrist strap or a strap around a hand. In another embodiment, the pulse oximeter sensor 212 is combined with a heart sensor 202. In yet another embodiment, the pulse oximeter sensor 212 uses a camera lens on a smartphone or a tablet.

The body temperature sensor 214 measures core body temperature and/or skin temperature. The body temperature sensor 214 is a thermistor, an infrared sensor, or thermal flux sensor. In one embodiment, the body temperature sensor 214 is incorporated into the EMS device. In another embodiment, the body temperature sensor 214 is incorporated into an armband, a wristband, a patch, or a bandage. In yet another embodiment, the body temperature sensor 214 is an ingestible core body temperature sensor (e.g., COR-TEMP®). The body temperature sensor 214 is preferably wireless.

The analyte sensor 216 monitors levels of at least one analyte in blood, sweat, or interstitial fluid. In one embodiment, the at least one analyte is an electrolyte, a small molecule (molecular weight <900 Daltons), a protein (e.g., C-reactive protein), an enzyme, and/or a metabolite. In another embodiment, the at least one analyte is glucose, lactate, lactic acid, creatine kinase, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 216 is preferably non-invasive. Alternatively, the analyte sensor 216 is minimally invasive or implanted. In one embodiment, the analyte sensor 216 is incorporated into a wearable device. Alternatively, the analyte sensor 216 is incorporated into a patch or a bandage.

The pH sensor 218 measures a pH level of the sweat of the user. In a preferred embodiment, the pH sensor 218 is wireless. In one embodiment, the pH sensor 218 is incorporated into a wearable device, a patch, or a bandage. Alternatively, the pH sensor 218 is incorporated into the EMS device.

In one embodiment, the blood pressure (BP) sensor 220 is a sphygmomanometer. The sphygmomanometer is preferably wireless. Alternatively, the blood pressure sensor 220 estimates the blood pressure without an inflatable cuff (e.g., SALU™ Pulse+). In one embodiment, the blood pressure sensor 220 is incorporated into a wearable device.

The electrodermal activity sensor 222 measures sympathetic nervous system activity. In one embodiment, the electrodermal activity sensor 222 is incorporated into a wearable device. Alternatively, the electrodermal activity sensor 222 is incorporated into a patch or a bandage.

The body weight sensor 224 is preferably a smart scale (e.g., FITBIT® ARIA®, NOKIA® Body+, GARMIN® INDEX™, UNDER ARMOUR® Scale, PIVOTAL LIVING® Smart Scale, IHEALTH® Core). In another embodiment, a body mass index (BMI) of the user is calculated using the body weight of the user and the height of the user.

The hydration sensor 226 is preferably incorporated into a wearable device (e.g., LVL®, NIX®, GOBE2@). Alternatively, the hydration sensor 226 is a bioimpedance device (e.g., INBODY™ 770).

The GPS sensor 228 is operable to detect a GPS location of the user. In one embodiment, the GPS sensor 228 is incorporated in a wearable device, a patch, or a bandage. Alternatively, the GPS sensor 228 is incorporated into the EMS device. Data from the GPS sensor 228 is operable to determine a total distance traveled by the user.

The pressure sensor 230 is operable to measure a pressure distributed by the body. In a preferred embodiment, the pressure sensor 230 is incorporated into a platform (e.g., EPS+R by Loran Engineering).

The spinal sensor 232 is preferably operable to measure a shape and a length of the spine. An example of a spinal sensor is described in U.S. Pat. No. 6,637,278, which is incorporated herein by reference in its entirety.

Environmental Sensors

The environmental temperature sensor 234 measures a temperature of the environment. In one embodiment, the environmental temperature sensor 234 is incorporated into an automation system. In another embodiment, the environmental temperature sensor 234 is incorporated into the EMS device.

The humidity sensor 236 measures a temperature of the environment. In one embodiment, the humidity sensor 236 is incorporated into an automation system. Alternatively, the humidity sensor 234 is incorporated into the EMS device.

The motion sensor 238 is preferably a non-contact sensor. In one embodiment, the motion sensor 238 includes at least one camera to detect movement of at least one user. The server and/or the computing device is preferably operable to use data from the at least one camera to analyze a user's form.

Server

The server is continuously updated with the global historical objective data 240, the global historical subjective data 242, the global historical environmental data 244, and the global profile data 246.

In one embodiment, the server includes a classification engine operable to classify the global historical objective data 240, the global historical subjective data 242, the global historical environmental data 244, and the global profile data 246. The classification is based on gender, age range, goals, etc.

In one embodiment, the server includes a modeling engine operable to build a training program based on a machine learning algorithm. The machine learning algorithm is operable to continuously extract data regarding training programs and/or exercises from various databases and/or data sources.

In one embodiment, the server platform includes a reasoning engine built with artificial intelligence (AI) algorithms. The reasoning engine is operable to generate a reasoning model based on multiple sets of training data. The multiple sets of training data are a subset of historical data. For example, a user's fitness is significantly improved after a specific training program is performed for a predetermined period of time. The training data includes context data (e.g., baseline data) and action data (e.g., data from training sessions). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

Computing Device

As previously described, the at least one computing device (e.g., smartphone, tablet, computer) includes at least one processor, an analytics engine, a control interface, a user interface, and a local storage. The local storage includes a user profile, historical subjective data, historical objective data, and historical environmental data. The at least one computing device is preferably operable to communicate with the at least one server and/or the control unit via wireless communication. Examples of wireless communication interfaces include, but are not limited to, an Intranet connection, Internet, ISM, BLUETOOTH® technology, WI-FI®, WIMAX®, IEEE 802.11 technology, radio frequency (RF), Near Field Communication (NFC), ZIGBEE®, Infrared Data Association (IrDA) compatible protocols, Local Area Networks (LAN), Wide Area Networks (WAN), Shared Wireless Access Protocol (SWAP), any combinations thereof, and other types of wireless networking protocols.

In a preferred embodiment, the at least one computing device (e.g., smartphone, computer, tablet) includes a mobile application. The mobile application provides a graphical user interface (GUI) operable for entering and storing information (e.g., user profile). In another embodiment, the mobile application is operable to select, monitor, and set a particular training application for the system. The GUI preferably provides a historical view of changes over time, allowing a user to visualize progress.

In a preferred embodiment, the mobile application is operable to obtain data from at least one third party application (e.g., APPLE® Health, MYFITNESSPAL®, FITBIT®, nutrition tracker). Advantageously, the at least one third party application may provide information about a user's health and/or lifestyle while not performing the exercise. In one embodiment, the machine learning component utilizes the additional information to further suggest changes to the user's exercise routine and/or the user's diet.

In one embodiment, the server provides licensed access to the mobile application via an application program interface (API). A user account is created based on a type of user (e.g., administrative staff, trainer, supervisor, individual). User identification is required to access global historical subjective data, global historical objective data, global historical environmental data, and/or global profile data. In one embodiment, biometric data is used for user authentication (e.g., facial features, fingerprint, heartbeat, vein recognition). In another embodiment, a password is used for user authentication.

Training Programs

In one embodiment, the server provides a training program for a user. The training program is accessible by a user when the user logs into their account. In one embodiment, the training program is a pre-determined program focusing on at least one muscle and/or at least one muscle group (e.g. work biceps and hamstrings at the same time).

In another embodiment, at least one training program is recommended by the AI component. This recommendation is based on attributes including a user's historical data, user profile, specified area(s) of the body and/or muscle group(s) a user wants to improve, goals, and/or trainer input. In one embodiment, the AI component automatically selects a training program from the at least one recommended training program(s).

In another embodiment, the training program is accessible through the EMS control unit. In one embodiment, a trainer and/or user selects the user's desired program or a trainer's recommended program. In addition, parameters of the training program are automatically adjusted by the AI-component based on real-time user data. Alternatively, the parameters of the training program are manually adjusted as the training program is performed.

An effectiveness of the training program is measured by evaluating progress with user goals including, but not limited to, goals related to a weight of a user, at least one user measurement (e.g., waist circumference), a body fat percentage of the user, and/or a visceral fat of the user. Additionally, the effectiveness of the training is measured based on changes, including, but not limited to, increases in muscle strength, power, flexibility, endurance, balance, speed, agility, and/or cardiovascular strength.

Tests for muscle strength include, but are not limited to, one repetition maximum (1-RM), deadlift repetition max, muscle fiber RM, isokinetic strength, finger pinch grip, abdominal strength, dynamic sit-up, trunk lift, straight leg ab strength, isometric back strength, isometric leg strength, isometric leg extension, push and pull strength, upper back strength, and/or lower back strength.

Tests for power include, but are not limited to, vertical jump, medicine ball throw test, Magaria Kalamen Power Test, Wingate Test for anaerobic capacity, burpees, 30 meter sprints, and/or standing broad jump test.

Flexibility is measured directly or indirectly. Indirect flexibility tests involve the linear measurement of distances between segments or from an external object. Indirect flexibility tests include, but are not limited to, a sit and reach test, v-sit test, floor touch test, groin flexibility test, calf muscle flexibility test, side-bending test, trunk rotation tests, shoulder rotation, and/or shoulder flexion. Direct flexibility methods measure angular displacements between adjacent segments or from an external reference. Direct flexibility tests include, but are not limited to, an Active Knee Extension (AKE) Hamstring flexibility test, straight leg raise, and/or a Modified Thomas test (assessing hip flexibility, specifically of the iliopsoas and quadriceps muscles).

Tests for endurance include, but are not limited to, the Astrand treadmill test, the 2.4 km run test, the multistage bleep test (a continuous sub-maximal test involving a 20 m shuttle run), and/or the Cooper 1.5-mile walk-run test.

Balance tests include, but are not limited to, a timed one foot (leg) standing balance assessment. A user is timed until the user changes position of their arms (crossed in front of the chest), trunk (greater than forty-five degrees off center), moves the stationary leg, and/or lowers the raised foot to touch the floor. Balance can also be measured dynamically using tandem walking (walking heel to toe without deviating from a straight line) and/or a one-legged standing balance test while moving the raised leg forward, to the side, and backwards.

Tests for speed include, but are not limited to, sprints (e.g., 30 yard dash, 20 meter dash, 30 meter dash, 40 yard dash, 40 meter sprint, 50 meter sprint, 60 yard dash, 60 meter sprint), the cycling 40 meter sprint test, the swimming 100 meter test, the pale tapping test (upper body speed), and/or the 10×5 meter shuttle test.

Tests for agility include, but are not limited to, the Illinois agility run test, a 25 yard shuttle run, the Zig Zag test, the Figure-of-Eight agility run test (a user runs around two cones placed 10 meters apart), the 505 agility test (the user dribbles a soccer ball through a course made up of markers spaced 5 and 15 meters from a line marked on the ground), the Hexagon test, the quadrant jump test, the T-test (forward, lateral, and backwards running), a 10 meter shuttle run, the Edgren Side Step test, and/or a 20 yard shuttle run.

Cardiovascular strength is evaluated via methods including, but not limited to, using a heart rate monitor (e.g., ensuring a user is working within a predesignated target heart rate zone), measuring a maximum rate of oxygen consumption ($VO_2$ max), the three-minute step test, and/or the Rockport walk test.

Stretch-Shortening Cycle

The stretch-shortening cycle (SSC) is an eccentric contraction of a muscle (elongation under contraction) followed by a concentric contraction (muscle shortening contraction). One example of an SSC is squatting and then standing. In this case, the primary muscle group is the quadriceps. The squatting portion is stretch phase of the cycle and the standing portion is the shortening phase of the cycle. Additional information regarding the SSC is found in Seiberl, Wolfgang et al. "The stretch-shortening cycle (SSC) revisited: residual force enhancement contributes to increased performance during fast SSCs of human m. adductor pollicis" *Physiological reports* vol. 3,5 (2015): e12401, which is incorporated herein by reference in its entirety.

Agonist and antagonist muscle groups work in opposition while the electrical current of the EMS control unit is on. The SSC is used for both lower body and upper body exercises while the user is attached to the EMS control unit. Example SSC exercises performed while attached to the EMS control unit include, but are not limited to, slow squats, deep squats, arm extensions and flexions, pectoral flys, back arches and bows, overhead presses, push-ups, sit-ups, lateral leg slides with foot pad, vertical jumps, and/or chest presses. In one embodiment, the SSC exercise is augmented with weighted bars, weights, and/or elastic bands.

Functional Fitness

In one embodiment, a functional fitness training program is selected to provide benefits related to a specific sport (e.g., hockey, golf, baseball, tennis, basketball, soccer, racing, track). In one embodiment, the user interacts with a piece of sports equipment (e.g., hockey stick, golf club, baseball bat, tennis racket, baseball, soccer ball, basketball). In another embodiment, the user performs a specific training program relating to the piece of sports equipment and an action the user wants to improve upon (e.g., golf swing, tennis serve, baseball swing).

In one example, the EMS device and the EMS control unit are used by a user who wants to strengthen a particular muscle or set of muscles relating to golf. In this example, a user may practice various training programs wherein the user is holding a golf club and/or simulating the holding of a golf club while wearing the EMS device. The EMS control unit is operable to be automatically or manually adjusted, through either feedback from the body sensors and/or the machine learning component to create a training program specifically for golf.

In another embodiment, a functional fitness training program incorporates exercises using a hockey stick. The functional fitness training program focuses on at least one muscle and/or at least one muscle group related to improving a user's swing, flexibility, power, strength, endurance, form, reaction time, and/or coordination. Further, the training program includes vertical pull training (e.g., all variations of pull-ups, all variations of chin ups, all variations of lateral pulldowns), horizontal pull training (e.g., Barbell row, Pendlay row, Rope face pulls, one or two arm Dumbbell row, seated cable rows, chest supporting rowing), practice shot training programs (e.g., a user takes a desired or recommended number of swings with varying levels of pulse frequencies), and form training programs (e.g., a user runs through stages of a user selected, trainer selected, and/or AI-component selected swing type). This specific training program allows a user to train the relevant muscle groups through a combination of functional fitness and standard training programs. A user's progress in this training program includes measurements of a user's swing speed, form deviation, reaction time, flexibility, and/or shot power (e.g., once a user's hockey stick makes contact with another object).

In another embodiment, a functional fitness training program incorporates exercises using a basketball. This training program includes training relating to perfecting movement and mechanics, increasing a user's speed of movement and mechanics, maximizing a user's ability to produce and control force, and/or improve a user's ability to sustain and recover from bouts of exercise. Further, the training program includes Olympic lifts (e.g., Clean and Jerk, Snatch, Hang Clean, High Pulls), squats (e.g., Barbell back squat, front squat), deadlifts, push-ups, pull-ups, glute-ham raises (strengthening the hamstrings), rear foot elevated split squats (lower-body strength exercise), French press (working the triceps), anti-rotation holds (core strength), and/or calf raises (increasing a user's vertical jump and ankle strength). A user's progress in a training program specific to the sport of basketball measures a user's vertical jump, reaction time, ball control, endurance, and/or speed.

In another embodiment, a functional fitness training program includes exercises using a baseball (e.g., throw, catch) and/or a baseball bat. Further, the training program includes explosive exercises (e.g., power cleans, hang cleans), lower-body exercises (e.g., squats, lunges, step-ups, deadlifts), rotational core exercises (e.g., medicine ball slams, medicine ball jump slams, medicine ball wall punches, medicine ball rotational throws, medicine ball woodchoppers), hip exercises (e.g., standing leg raises, knee tucks, single-leg hip raises, glute-ham raises), and/or upper-body exercises (e.g., push-ups, pull-ups, chin-ups, dips, inverted rows, physioball push-ups). A user's progress in this program is based on flexibility, endurance, swing speed (i.e., how fast a user swings a baseball bat), throw speed (i.e., how fast a user throws a baseball), and/or reaction time.

In another embodiment, a functional fitness training program incorporates exercises using a football (e.g., kick, throw, catch). Further, the training program includes weight training exercises such as barbell squats, dumbbell squats, sled hack squats, dumbbell incline bench press, Romanian deadlift, dumbbell biceps arm curl, dumbbell triceps extension, seated cable row, lateral pulldown, reverse crunches, barbell hack squats, barbell front squats, barbell bench press, pull-ups, military (overhead) press, barbell hang cleans, cable push and pull, barbell push press, and/or incline machine rows. A user's progress in this program is measured by strength, hypertrophy (i.e., building muscle size), power (i.e., moving heavy objects in a short period of time), and/or speed.

In another embodiment, a functional fitness training program incorporates exercises using a soccer ball (e.g., pass, drop kick, overhead throw). Further, the training program includes ankle mobility exercises, lateral jumps (increasing ankle mobility, hip joint and/or core strength), suspended lunge with hops (dynamic exercises activating fast-twitch muscle fibers), side shuffles (improves movement coordination), bunny hops (maximize activation of receptors, increase mobility, improve blood circulation, improve respiration), high hurdle jump (a plyometric exercise with an obstacle), single-leg balance (balancing on a disk pillow and volley kicking a soccer ball), standing cable lifting, side plank and row with band, half-kneeling cable chop, anti-rotational press (from a tall-kneeling position with a band), and/or single-leg step up (using an unstable platform).

In another embodiment, a functional fitness program specific to tennis incorporates exercises using a tennis racket (e.g., serve, forehand, backhand, volley). Further, the functional fitness program incorporates shoulder exercises (e.g., shoulder press, lateral raise, forward raise, shoulder joint), rotator cuff exercises (e.g., horizontal external rotations, external rotations with knee support, external rotations while lying on one side, internal rotations), elbow exercises (e.g., bicep curls, tricep extensions, forearm pronation and supination), wrist training (e.g., wrist curls, wrist extensions, wrist rotations, grips), upper-body exercises (e.g., bench press, push-ups, single arm dumbbell rows, a combination of free weights, dumbbell fly, peck deck machine fly, pull-ups, lateral pull downs), core exercises (e.g., crunches, twisting crunches, superman exercises, standing Russian twists), lower-body exercises (e.g., deadlifts, bent over rows, squats, machine leg presses, split squats, lunges, knee extensions, hamstring curls, calf raise), and/or plyometric exercises (e.g., step jumps, side jumps, ankle jumps, medicine ball exercises, chest throws, overhead throws, side throws). Progress in this training program includes measuring a user's power (e.g., how hard a user can hit a tennis ball), ball control, physique balance, possible joint and/or spine misalignments, and/or endurance.

In yet another embodiment, a functional fitness training program specific to racing (e.g., NASCAR, F1) includes simulated race conditions (e.g., steering wheel, pedals, gear shift, chair). This training program focuses on lighter weights and higher repetitions in order for a user to retain lean muscle instead of bulk. Further, the training program includes back squats, deadlifts, bench press, shoulder press, rows, pull-ups, push-ups, V-sits, sit-ups, planks, Swiss ball exercises (e.g., deficit push-ups, balancing), sledgehammer exercises (e.g., smashing tires), and/or tire exercises (e.g., flipping large tires, drive kettlebell swings). A user's progress in this program is based on a user's lean muscle retention, endurance, and/or strength.

Incorporation into or Use with Other Equipment

The EMS device and the EMS control unit can also be used in conjunction with an exercise machine. In one embodiment, the exercise machine is an elliptical, a stair climber, a bicycle (e.g., Spin bike), a vertical climber, a weight machine, a treadmill, a ski machine, a rowing machine, a glider, an incline trainer, a resistance machine (e.g., BOWFLEX), and/or a Pilates machine (e.g., reformer, Cadillac, chair). In another embodiment, the EMS control unit is incorporated into the exercise machine itself. In yet another embodiment, the exercise machine includes at least one entertainment option (e.g., audio player, music player, video screen, game console). In still another embodiment, the exercise machine includes a voice component to instruct a user to change at least one setting and/or inform a user that the exercise machine is automatically changing the at least one setting (e.g., change speed, the speed is changing, change resistance, the resistance is changing).

In one embodiment, the EMS control unit is used with a bicycle. A user wearing an EMS device links the EMS device with the EMS control unit and begins to pedal on the bicycle. In a preferred embodiment, the EMS control unit is connected to the bicycle. The EMS control unit stimulates a user's muscles (e.g., lower limbs, arms, abdominals, back) based on a user selected, trainer selected, and/or AI-component recommended training program. In one embodiment, the training program is further modified while a user is actively participating either automatically (via an AI component) or manually (user and/or trainer adjusted). Adjustments include, but are not limited to, seat height, speed level (revolutions per minute), resistance level (e.g., low, medium, high), and/or entertainment options.

Alternatively, the EMS control unit is integrated with the bicycle. A user wearing an EMS device links the EMS device with the bicycle that contains the EMS control unit (e.g., via a cable) and begins to pedal. This negates the need for a separate system that only handles EMS controls. In this aspect, a user wearing an EMS device has greater mobility since all EMS controls are handled through the bicycle exercise system. Once a user selects a desired training program, a trainer-recommended program, and/or an AI component recommended program, the training program can be further adjusted while a user is actively working towards the training program's completion. This adjustment can be made manually by the user and/or the trainer, or can be made automatically through the AI-component. Adjustments include seat height, speed level (revolutions per minute), resistance level (e.g., low, medium, high), heart rate monitor (alerts a user when they fall outside of a target zone), and/or entertainment options (e.g., MP3 player, video screen, game console).

In another embodiment, the EMS control unit interacts with a rowing exercise system. A user wearing an EMS device links the EMS device with the EMS control unit and begins to row. In a preferred embodiment, the EMS control unit is connected to the rowing machine. The EMS control unit controls the settings on the rowing machine relating to a user's training program. The EMS control unit is operable to adjust the rowing machine's resistance settings to match the training program. For example, air resistance (good for high intensity interval training and CrossFit workouts) enables a user to row intensely for one sitting and then easy the next. Additional settings include hydraulic-piston (enables independent workout for each of a user's arms), magnetic, water (determined by rowing intensity), and/or combinations thereof.

In another embodiment, the EMS control device is integrated into the rowing exercise system. A user wearing an EMS device links with the control device of the rowing exercise system and begins to row. With the direct link created between the EMS device and the rowing exercise system, the AI-component automatically adjusts various settings (e.g. air resistance, hydraulic piston resistance, magnetic resistance, water resistance) based on a user's current performance of the training program (using real-time user information). Alternatively, the user and/or the trainer manually adjusts the settings.

In another embodiment, the EMS control unit interacts with an elliptical machine or a treadmill. The user wearing the EMS device links with the EMS control unit. In a preferred embodiment, the EMS control unit is connected to the elliptical machine or the treadmill. The AI component is operable to automatically adjust various settings (e.g. incline or decline, steps per minute, speed etc.) based on a user's current performance of the training program (using real-time user information). Alternatively, the user and/or the trainer manually adjusts the settings.

Figure 3:
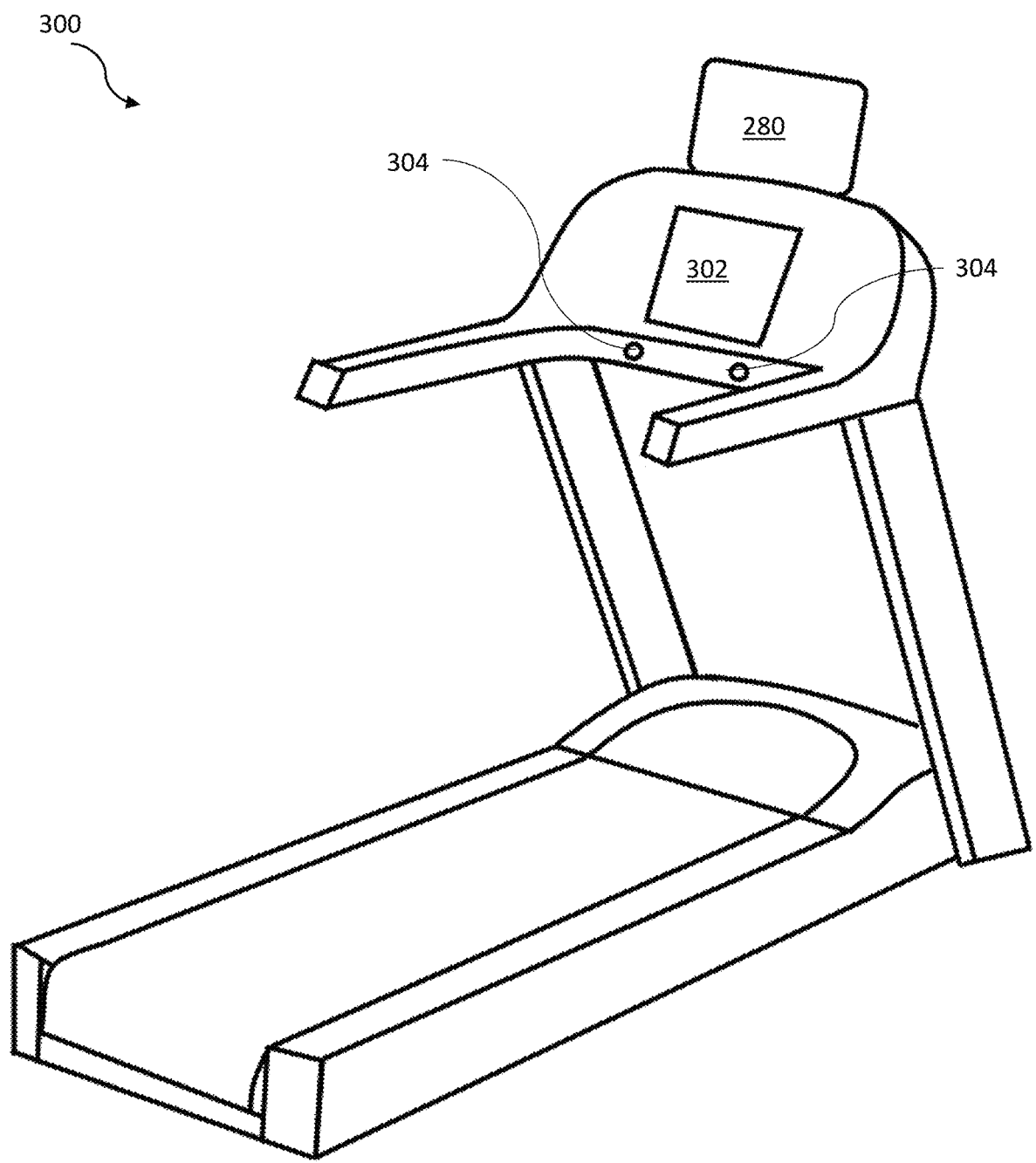
FIG. 3 illustrates one embodiment of the present invention where the EMS control unit is incorporated into a treadmill.

FIG. 3 illustrates one embodiment of the present invention where the EMS control unit is incorporated into a treadmill 300. The treadmill 300 includes a first user interface 302 for adjusting treadmill settings (e.g., speed, incline, program). The treadmill 300 includes an EMS user interface 280. The EMS user interface 280 is preferably a touch screen that is operable to allow a user to select settings for the EMS control unit via the EMS control interface. In an alternative embodiment, the treadmill includes adjustable knobs, sliders, and/or dials. In one embodiment, the EMS user interface is removably attachable to the treadmill. The treadmill 300 includes at least one socket 304. Each of the signal cables for the EMS device includes a plug (not shown) that mates to a corresponding socket 304.

In yet another embodiment, the EMS control unit interacts with a Pilates machine (e.g., reformer, Cadillac). The user wearing the EMS device links with the EMS control unit and begins to exercise. In a preferred embodiment, the EMS control unit is connected to the Pilates machine. An AI component is operable to automatically adjust settings (e.g., resistance) based on a user's current performance of the training program (using real-time user information). Alternatively, the user and/or the trainer manually adjusts the settings.

Figure 4:
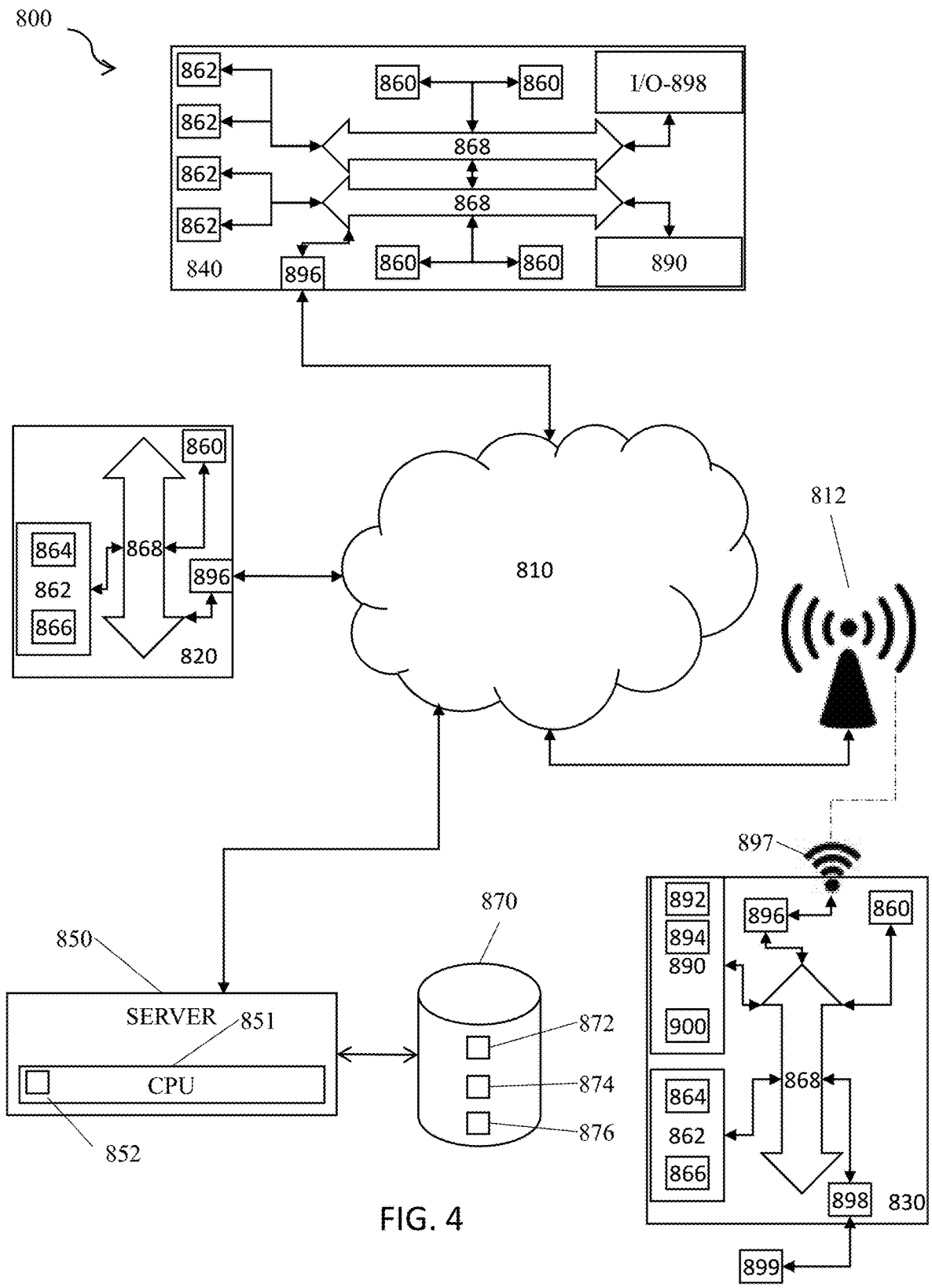
FIG. 4 is a schematic diagram of a cloud-based system of the present invention.

FIG. 4 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 4, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 4, may include other components that are not explicitly shown in FIG. 4, or may utilize an architecture completely different than that shown in FIG. 4. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. An electrical muscle stimulation system comprising:
at least one electrical muscle stimulation device;
at least one body sensor;
at least one environmental sensor;
an electrical stimulation control unit;
a computing device; and
a server;
wherein the at least one body sensor and the at least one environmental sensor are operable to collect data;
wherein the at least one body sensor is operable to transmit the data to the electrical stimulation control unit;
wherein the at least one environmental sensor is operable to transmit the data to the electrical stimulation control unit;
wherein each of the at least one electrical muscle stimulation device includes at least one electrode configured to deliver electrical impulses from the electrical stimulation control unit;
wherein the electrical stimulation control unit includes at least one processor to analyze the data, at least one transceiver to obtain the data, at least one local storage to store the data, and a user interface to display the data to the user;
wherein the at least one electrical muscle stimulation device further includes a heating and/or cooling device to provide a heating and/or cooling level;
wherein the electrical stimulation control unit automatically adjusts the heating and/or cooling level provided by the heating and/or cooling device of the at least one electrical muscle stimulation device in response to the data received from the at least one body sensor and/or the at least one environmental sensor;
wherein the electrical stimulation control unit is operable to determine and adjust at least one setting of an exercise machine based on data captured from one or more of the at least one body sensor and/or the at least one environmental sensor;
wherein the local storage includes a training program;
wherein the electrical stimulation control unit is in network communication with the at least one electrical muscle stimulation device, the server, the at least one body sensor, the at least one environmental sensor, and the computing device;
wherein the server is in network communication with the computing device, the at least one body sensor, the at least one environmental sensor, and the at least one electrical muscle stimulation device; and
wherein the server is operable to store the data from the at least one body sensor and the at least one environmental sensor.

2. The electrical muscle stimulation system of claim 1, wherein the local storage includes user profile data, historical subjective data, historical objective data, and/or historical environmental data.

3. The electrical muscle stimulation system of claim 1, further including at least one wearable device, wherein one or more of the at least one body sensor and the at least one environmental sensor is incorporated into the at least one wearable device.

4. The electrical muscle stimulation system of claim 1, wherein the at least one body sensor includes at least one heart sensor, at least one respiration sensor, at least one body composition sensor, at least one movement sensor, at least one electromyography sensor, at least one pulse oximetry sensor, at least one body temperature sensor, at least one analyte sensor, at least one pH sensor, at least one blood pressure sensor, at least one electrodermal activity sensor, at least one weight sensor, at least one hydration sensor, at least one GPS sensor, at least one pressure sensor, and/or at least one spinal sensor.

5. The electrical muscle stimulation system of claim 1, wherein the at least one environmental sensor includes a temperature sensor, a humidity sensor, and/or a motion sensor.

6. The electrical muscle stimulation system of claim 1, wherein the electrical stimulation control unit is configured to change an impulse signal type, an impulse signal frequency, an impulse signal intensity, an impulse signal polarity, an impulse signal duration, and/or a rest period between impulses for the electrical impulses delivered to the electrode.

7. The electrical muscle stimulation system of claim 6, wherein the electrical stimulation control unit is operable to automatically adjust the electrical impulses in response to the data received from one or more of the at least one body sensor and/or the at least one environmental sensor.

8. The electrical muscle stimulation system of claim 1, wherein the server is configured to determine an effectiveness of the training program, and wherein the effectiveness is determined by the server through comparative analysis of data acquired by the at least one body sensor and/or the at least one environmental sensor.

9. The electrical muscle stimulation system of claim 1, wherein the electrical stimulation control unit is configured to update the training program in real time and/or near real time in response to the data received from the at least one body sensor and/or the at least one environmental sensor.

10. The electrical muscle stimulation system of claim 1, wherein the training program is a sport specific training program, wherein the electrical stimulation control unit is configured to generate the sport specific training program, wherein the sport specific training program targets at least one muscle and/or at least one muscle group, wherein the at least one electrical muscle stimulation device is configured to stimulate the at least one muscle and/or the at least one muscle group, and wherein the electrical stimulation control unit is configured to automatically adjust the sport specific training program in response to the data received from one or more of the at least one body sensor and/or the at least one environmental sensor.

11. The electrical muscle stimulation system of claim 1, wherein the at least one electrical muscle stimulation device includes a one-piece suit.

12. The electrical muscle stimulation system of claim 1, wherein the at least one body sensor includes at least one heart sensor, at least one respiration sensor, at least one body composition sensor, at least one accelerometer, at least one electromyography sensor, at least one pulse oximeter, at least one analyte sensor, at least one pH sensor, at least one body weight sensor, at least one GPS sensor, and/or at least one spinal sensor.

* * * * *